(12) United States Patent
Horikoshi et al.

(10) Patent No.: US 9,434,739 B2
(45) Date of Patent: Sep. 6, 2016

(54) SYSTEMIC INSECTICIDE

(75) Inventors: Ryo Horikoshi, Yokohama (JP); Mitsuyuki Yabuzaki, Mishima (JP); Shinji Sakurai, Yokohama (JP); Kazuhiko Oyama, Higashimurayama (JP); Masaaki Mitomi, Yokosuka (JP)

(73) Assignee: MEIJI SEIKA PHARMA CO., LTD., Tokyo-To (JP)

( * ) Notice: Subject to any disclaimer, the term of this patent is extended or adjusted under 35 U.S.C. 154(b) by 149 days.

(21) Appl. No.: 12/809,755

(22) PCT Filed: Dec. 19, 2008

(86) PCT No.: PCT/JP2008/073165
§ 371 (c)(1),
(2), (4) Date: Jun. 21, 2010

(87) PCT Pub. No.: WO2009/081851
PCT Pub. Date: Jul. 2, 2009

(65) Prior Publication Data
US 2010/0281584 A1 Nov. 4, 2010

(30) Foreign Application Priority Data
Dec. 21, 2007 (JP) .................................. 2007-329998

(51) Int. Cl.
C07D 493/04 (2006.01)
A01N 25/00 (2006.01)
A01N 43/90 (2006.01)
A01N 25/02 (2006.01)

(52) U.S. Cl.
CPC ............ *C07D 493/04* (2013.01); *A01N 25/00* (2013.01); *A01N 25/02* (2013.01); *A01N 43/90* (2013.01)

(58) Field of Classification Search
CPC .... C07D 493/04; A01N 25/00; A01N 43/90; A01N 25/02
USPC ....................................................... 504/101
See application file for complete search history.

(56) References Cited

U.S. PATENT DOCUMENTS

| 5,807,721 | A | 9/1998 | Omura et al. |
| 7,491,738 | B2 | 2/2009 | Goto et al. |
| 2006/0135564 | A1 | 6/2006 | Kim et al. |
| 2006/0281780 | A1 | 12/2006 | Goto et al. |
| 2010/0281584 | A1 | 11/2010 | Horikoshi et al. |

FOREIGN PATENT DOCUMENTS

| AU | 2006253364 B2 * | 9/2013 |
| EP | 2107060 A1 * | 10/2009 |
| EP | 2 119 361 | 11/2009 |
| JP | 4-360895 | 12/1992 |
| JP | 8-259569 | 10/1996 |
| JP | 8-269062 | 10/1996 |
| JP | 2006-513233 | 4/2006 |
| RU | 2 492 649 | 1/2012 |
| TW | 200721978 | 6/2007 |
| WO | 94/09147 | 4/1994 |
| WO | WO 2004060065 A1 * | 7/2004 |
| WO | 2006/129714 | 12/2006 |
| WO | 2008/013336 | 1/2008 |
| WO | 2008/066153 | 6/2008 |

OTHER PUBLICATIONS

Chew. Definition [online]. The Free Dictionary, 2014 [retrieved on Sep. 4, 2014]. Retrieved from the Internet:<http://www.thefreedictionary.com/chew> 1 page.*
Ingest. Definition [online]. The Free Dictionary, 2014 [retrieved on Sep. 4, 2014]. Retrieved from the Internet:<http://www.thefreedictionary.com/ingest> 1 page.*
Schneider, Michael, Hemipteran Pests. [online]. Key to the Forest Insect Pests of Papau New Guinea, 1999 [retrieved on 20014-09-04]. Retrieved from the Internet:<http://www.fzi.uni-freiburg.de/InsectPestKey-long%20version/hemipter.htm> 1 page.*
International Preliminary Report on Patentability and Written Opinion of the International Searching Authority mailed Jul. 29, 2010 in corresponding International (PCT) Application No. PCT/JP2008/073165.
Supplementary European Search Report issued Dec. 13, 2011 in corresponding European Application No. 08865272.2.
International Search Report issued Feb. 10, 2009 in International (PCT) Application No. PCT/JP2008/073165.
Omura et al., "Pyripyropenes, Highly Potent Inhibitors of Acyl-CoA: Cholesterol Acyltransferase Produced by *Aspergillus fumigatus*", The Journal of Antibiotics, vol. 46, No. 7, pp. 1168-1169, Jul. 1993.

(Continued)

*Primary Examiner* — John Pak
*Assistant Examiner* — Andriae M Holt
(74) *Attorney, Agent, or Firm* — Wenderoth, Lind & Ponack, L.L.P.

(57) ABSTRACT

Disclosed are compounds that are utilizable as systemic insecticides and possess excellent systemic properties. Compounds represented by formula (1) have excellent systemic insecticidal activity. Accordingly, a composition comprising as an active ingredient the compound of formula (1) or salt thereof is useful as a systemic insecticide.

[Chemical formula 1]

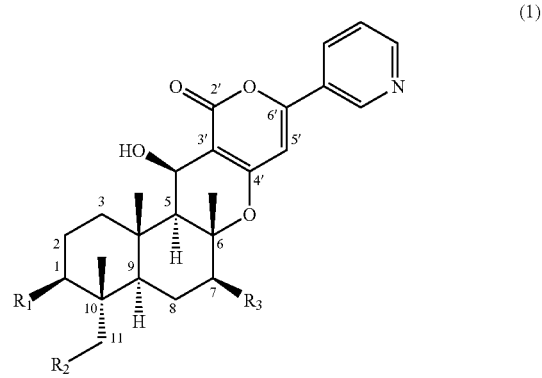

(1)

5 Claims, No Drawings

(56) References Cited

OTHER PUBLICATIONS

Hui-Juan Wang et al., "Aflavinines and Other Antiinsectan Metabolites from the Ascostromata of *Eupenicillium crustaceum* and Related Species", Applied and Environmental Microbiology, vol. 61, No. 12, pp. 4429-4435, 1995.

Toshiaki Sunazuka et al., "Synthetic Study of α-Pyrone Meroterpenoids, Pyripyropens", Journal of Synthetic Organic Chemistry, vol. 56, No. 6, pp. 478-488, 1998.

Yamashita et al., "Nouyaku No Kagaku (The Science of Agricultural Chemicals)", Buneido Publishing Co., Ltd., p. 14, 1966.

Taiwanese Office Action issued Jan. 29, 2013 in corresponding Taiwanese Patent Application No. 097149799 with English translation.

Office Action issued May 22, 2013 in corresponding Australian Application No. 2008342070.

Written Opinion issued Mar. 12, 2014 in corresponding Vietnamese Application No. 1-2010-01881, with English language translation thereof.

Notification of Reason for Rejection issued Jun. 20, 2014 in Japanese Application No. 2009-547072, with English language translation.

* cited by examiner

SYSTEMIC INSECTICIDE

CROSS-REFERENCE TO RELATED APPLICATIONS

The application is based upon and claims the benefit of priority from the prior Japanese Patent Application No. 329998/2007, filed on Dec. 21, 2007; the entire contents of which are incorporated herein by reference.

BACKGROUND OF THE INVENTION

1. Field of Invention

The present invention relates to an agricultural or horticultural composition for use as a novel systemic insecticide, and a control method using the same.

2. Background Art

The positive list system for residual agricultural chemicals and the like has recently come into effect, and a great deal of interest has been drawn to measures for prevention of drift of agricultural chemicals and the like. Unlike the conventional foliage application technology, systemic chemicals are usually applied, for example, to soil or nursery boxes for insect pest control purposes and thus can reduce drift of the chemicals into a surrounding environment. Also from the viewpoints of labor saving and ensuring of safety for agricultural chemical application, systemic insecticides are superior to the conventional foliage application technology. For example, since the insecticidal effect can be attained only by applying a systemic insecticide to plant nursery boxes, work necessary for agriculture workers to spend in chemical treatment can be suppressed. Further, systemic insecticides can be properly applied to crops and thus can prevent exposure of persons, who apply agricultural chemicals, to agricultural chemicals. Accordingly, systemic insecticides are also superior in ensuring safety. Furthermore, also from the viewpoint of efficacy, formulations having a longer residual activity than formulations for foliage application can be provided by adding, for example, release control properties to formulations containing a systemic insecticide. By virtue of the usefulness of systemic insecticides, the development of systemic insecticides as agricultural or horticultural technology different from conventional foliage application technology or the like mainly in paddy rice and vegetable markets has recently been expected.

On the other hand, WO 2004/060065 and Applied and Environmental Microbiology (1995), 61(12), 4429-35 describe that pyripyropene A has insecticidal effect against *Plutella xylostella*, *Tenebrio molitor*, and *Helicoverpa armiger*.

Further, WO 2006/129714 describes that a group of pyripyropene compounds including compounds of formula (1) has an insecticidal activity against *Myzus persicae* Sulzer, *Trigonotylus caelestialium*, *Plutella xylostella*, and *Helicoverpa armigera*. Furthermore, Japanese Patent Application Laid-Open No. 360895/1992, Journal of Antibiotics (1993), 46(7), 1168-69, Journal of Synthetic Organic Chemistry, Japan (1998), vol. 56, No. 6, pp. 478-488, WO 94/09147, Japanese Patent Application Laid-Open No. 259569/1996, and Japanese Patent Application, Laid-Open No. 269062/1996 describe pyripyropenes, which are naturally occurring products or derivatives thereof, and their inhibitory activity against ACAT (acyl CoA: cholesterol acyltransferase).

A plurality of literatures report the insecticidal activity of compounds related to pyripyropene. They, however, describe neither the fact that, among the compounds related to pyripyropene, a group of specific compounds has systemic properties, nor use of the group of specific compounds as systemic insecticides.

Up to now, a number of systemic insecticides have been reported. For all of them, however, drug resistant species and uncontrollable species exist, and the development of novel insecticides having high systemic control effect has been desired still.

SUMMARY OF THE INVENTION

The present inventors have now found that compounds represented by formula (1) or salts thereof have high systemic control effect. The present invention has been made based on such finding.

Accordingly, an object of the present invention is to provide a chemical which can be effectively and safely used for agricultural or horticultural applications and has high systemic properties, and a control method using the same.

According to the present invention, a systemic insecticide comprises as active ingredients one or more compounds represented by formula (1) or salts thereof:

[Chemical formula 1]

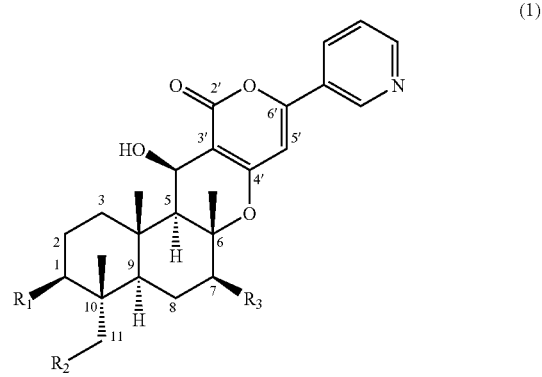

wherein
$R_1$ represents hydroxyl,
  optionally substituted $C_{1-6}$ alkylcarbonyloxy,
  optionally substituted $C_{2-6}$ alkenylcarbonyloxy, or
  optionally substituted $C_{2-6}$ alkynylcarbonyloxy;
$R_2$ represents a hydrogen atom,
  hydroxyl,
  optionally substituted $C_{1-6}$ alkylcarbonyloxy,
  optionally substituted $C_{2-6}$ alkenylcarbonyloxy, or
  optionally substituted $C_{2-6}$ alkynylcarbonyloxy; and
$R_3$ represents a hydrogen atom,
  hydroxyl,
  optionally substituted methylcarbonyloxy, or
  oxo in the absence of a hydrogen atom at the 7-position.

According to the present invention, there is also provided a method for controlling agricultural or horticultural insect pests, the method comprising:

applying an effective amount of one or more compounds represented by formula (1) or salts thereof to an object selected from the group consisting of soil, nutrient solution in nutriculture, solid medium in nutriculture, and seed, root, tuber, bulb, and rhizome of a plant; and systemically translocating the compounds represented by formula (1) into a plant.

DETAILED DESCRIPTION OF THE INVENTION

Definition

The agent having systemic properties (known also as "systemic insecticide") as used herein means an agent that can be systemically translocated into a plant and can poison pests, which suck or chew the plant to death (see New edition "Nouyaku No Kagaku (The Science of Agricultural Chemicals)" (BUNEIDO PUBLISHING CO., LTD, Kyohei Yamashita et al.), p. 14).

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, "$C_{1-6}$" in "$C_{1-6}$ alkyl" as a group or a part of a group means that the number of carbon atoms in the alkyl group is 1 to 6 and that, in the case of cyclic alkyl, the number of carbon atoms is at least three.

Further, the "optionally substituted" alkyl as used herein means that one or more hydrogen atoms on the alkyl group are optionally substituted by one or more substituents which may be the same or different. It will be apparent to a person having ordinary skill in the art that the maximum number of substituents may be determined depending upon the number of substitutable hydrogen atoms on the alkyl group. This is also true of alkenyl and alkynyl.

Compounds Represented by Formula (1) or Salts Thereof

The systemic insecticide according to the present invention comprises as an active ingredient a compound of formula (1) or a salt thereof. It is a surprising fact that compounds of formula (1) have high systemic insecticidal activity.

Preferably, in the compound of formula (1), "$C_{1-6}$ alkylcarbonyloxy" represented by $R_1$ and $R_2$ is $C_{1-4}$ alkylcarbonyloxy, more preferably acetyloxy, ethylcarbonyloxy, or $C_{3-4}$ cyclic alkylcarbonyloxy. The $C_{1-6}$ alkylcarbonyloxy group is optionally substituted, and examples of such substituents include halogen atoms, cyano, $C_{3-5}$ cycloalkyl, trifluoromethyloxy, or trifluoromethylthio. A halogen atom or $C_{3-5}$ cycloalkyl is preferred.

"Methylcarbonyloxy" represented by $R_3$ is optionally substituted, and examples of such substituents include halogen atoms, cyano, trifluoromethyl, or trifluoromethoxy, preferably a halogen atom or cyano.

Preferably, "$C_{2-6}$ alkenylcarbonyloxy" represented by $R_1$ and $R_2$ is $C_{2-4}$ alkenylcarbonyloxy. The $C_{2-6}$ alkenylcarbonyloxy group is optionally substituted, and examples of such substituents include halogen atoms, cyano, trifluoromethyloxy, or trifluoromethylthio.

Preferably, "$C_{2-6}$ alkynylcarbonyloxy" represented by $R_1$ and $R_2$ is $C_{2-4}$ alkynylcarbonyloxy. The $C_{2-6}$ alkynylcarbonyloxy group is optionally substituted, and examples of such substituents include halogen atoms, cyano, trifluoromethyloxy, or trifluoromethylthio.

In the compounds of formula (1), preferably, $R_1$ represents hydroxyl or optionally substituted $C_{1-6}$ alkylcarbonyloxy, more preferably hydroxyl or optionally substituted $C_{3-4}$ cyclic alkylcarbonyloxy.

Further, in the compounds of formula (1), preferably, $R_2$ represents optionally substituted $C_{1-6}$ alkylcarbonyloxy, more preferably optionally substituted $C_{3-4}$ cyclic alkylcarbonyloxy.

Furthermore, in the compounds of formula (1), preferably, $R_3$ represents hydroxyl, optionally substituted methylcarbonyloxy, or oxo in the absence of a hydrogen atom at the 7-position, more preferably hydroxyl.

According to a preferred embodiment of the present invention, in the compounds of formula (1), $R_1$ represents hydroxyl or optionally substituted $C_{1-6}$ alkylcarbonyloxy, and $R_2$ represents optionally substituted $C_{1-6}$ alkylcarbonyloxy.

According to another preferred embodiment of the present invention, in the compounds of formula (1), represents hydroxyl or optionally substituted $C_{1-6}$ alkylcarbonyloxy, and $R_3$ preferably represents hydroxyl, optionally substituted methylcarbonyloxy, or oxo in the absence of a hydrogen atom at the 7-position.

According to still another preferred embodiment of the present invention, in the compounds of formula (1), $R_2$ represents optionally substituted $C_{1-6}$ alkylcarbonyloxy, and $R_3$ represents hydroxyl, optionally substituted methylcarbonyloxy, or oxo in the absence of a hydrogen atom at the 7-position.

According to a more preferred embodiment of the present invention, in the compounds of formula (1), $R_1$ represents hydroxyl or optionally substituted $C_{1-6}$ alkylcarbonyloxy, $R_2$ represents optionally substituted $C_{1-6}$ alkylcarbonyloxy, and $R_3$ represents hydroxyl, optionally substituted methylcarbonyloxy, or oxo in the absence of a hydrogen atom at the 7-position.

According to another preferred embodiment of the present invention, in the compounds of formula (1), $R_1$ and $R_2$ represent optionally substituted $C_{3-4}$ cyclic alkylcarbonyloxy. According to another more preferred embodiment of the present invention, in the compounds of formula (1), $R_3$ represents hydroxyl. The compounds of formula (1) in the embodiments have significant systemic properties and can be particularly advantageously utilized for insect pest control applications.

More specifically, compounds 1 to 7 shown in Table 1 may be mentioned as preferred compounds of formula (1). In Table 1, substituents $R_1$, $R_2$, and $R_3$ correspond respectively to substituents $R_1$, $R_2$, and $R_3$ in formula (1).

TABLE 1

Test compounds in Test Example 3

| Compound No. | $R_1$ | $R_2$ | $R_3$ |
| --- | --- | --- | --- |
| 1 | OCOCH$_3$ | OCOCH$_3$ | OCOCH$_3$ |
| 2 | OCOCH$_3$ | OCOCH$_3$ | OH |
| 3 | OCOCH$_2$CH$_3$ | OCOCH$_2$CH$_3$ | OH |
| 4 | OCO-cyclopropyl | OCO-cyclopropyl | OH |
| 5 | OH | OCO-cyclopropyl | OH |
| 6 | OCO-cyclopropyl | OCO-cyclopropyl | O |
| 7 | OCO-cyclopropyl | OCO-cyclopropyl | H |

Further, in the present invention, salts of compounds of formula (1) are also usable, and examples, of such salts include agriculturally or horticulturally acceptable acid addition salts such as hydrochloride salts, nitrate salts, sulfate salts, phosphoric salts, or acetate salts.

Compounds of formula (1) including compounds shown in Table 1 and compounds shown in Table 6 used in Comparative Test Examples can be produced by processes described in Japanese Patent No. 2993767 (Japanese Patent Application Laid-Open No. 360895/1992), Japanese Patent Application Laid-Open No. 259569/1996, WO 2006/129714, and Japanese Patent No. 4015182, or processes based on the processes.

Systemic Insecticide

As described above, the compounds of formula (1) or salts thereof have high systemic insecticidal activity and can be advantageously utilized, for example, in control of insect pests that suck or chew plants. Thus, according to another aspect of the present invention, there is provided use of compounds represented by formula (1) or salts thereof, as a systemic insecticide.

Agricultural or horticultural insect pests against which the systemic insecticide according to the present invention has control effect include lepidopteran insect pests, for example, Noctuidae such as *Spodoptera litura, Spodoptera exigua, Pseudaletia separata, Mamestra brassicae, Agrotis ipsilon, Trichoplusia* spp., *Heliothis* spp., and *Helicoverpa* spp., Pyralidae such as *Chilo suppressalis, Cnaphalocrocis medinalis, Ostrinia nubilalis, Hellula undalis, Parapediasia teterrella, Notarcha derogata,* and *Plodia interpunctella,* Pieridae such as *Pieris rapae,* Tortricidae such as *Adoxophyes* spp., *Grapholita molesta,* and *Cydia pomonella,* Carposinidae such as *Carposina niponensis,* Lyonetiidae such as *Lyonetia* spp., Lymantriidae such as *Lymantria* ssp. and *Euproctis* spp., Yponomeutidae such as *Plutella xylostella,* Gelechiidae such as *Pectinophora gossypiella,* Arctiidae such as *Hyphantria cunea,* and Tineidae such as *Tinea translucens* Meyrick and *Tinea bissellinella;* hemipteran insect pests, for example, Aphididae such as *Myzus persicae* Sulzer and *Aphis gossypii,* Delphacidae such as *Laodelphax stratella, Nilaparvata lugens* Stal, and *Sogatella furcifera,* Cicadellidae such as *Nephotettix cincticeps* and *Empoasca onukii,* Pentatomidae such as *Trigonotylus caelestialium, Plautia crossota* stali, *Nezara viridula,* and *Riptortus clavatus,* Aleyrodidae such as *Trialeurodes vaporariorum* and *Bemisia tabaci,* Coccoidea such as *Pseudaulacaspis pentagona, Pseudococcus comstocki* Kuwana, and *Aonidiella aurantii,* Tingidae, and Psyllidae, Aphididae, Coccoidea, Aleyrodidae, and Cicadellidae being preferred; Coleoptera insect pests, for example, Curculionidae such as *Sitophilus zeamais, Lissorhoptrus oryzophilus,* and *Callosobruchus chinensis,* Tenebrionidae such as *Tenebrio molitor,* Scarabaeidae such as *Anomala cuprea* and *Anomala rufocuprea* Motschulsky, Chrysomelidae such as *Phyllotreta striolata, Aulacophora femoralis, Leptinotarsa decemlineata, Diabrotica virgifera virgifera,* and *Diabrotica undecimpunctata howardi,* Epilachna such as *Oulema oryzae* Kuwayama, *Paederus fuscipes,* Bostrychidae, and Epilachna *vigintioctopunctata* Fabricius, and Cerambycidae; Acari, for example, Tetranychidae such as *Tetranychus urticae* Koch, *Tetranychus kanzawai* Kishida, *Panonychus citri, Panonychus ulmi,* and *Oligonychus* spp., Eriophyidae such as *Aculops lycopersici, Aculops pelekassi* Keifer, and *Calacarus carinatus,* Tarsonemidae such as *Polyphagotarsonemus latus,* and Acaridae; hymenopteran insect pests, for example, Tenthredinidae such as *Athalia rosae ruficornis;* Orthopteran insect pests, for example, Acrididae; Dipteran insect pests, for example, Agromyzidae such as Muscidae, *Culex,* Anophelinae, Chironomidae, Calliphoridae, Sarcophagidae, Fanniidae, Anthomyiidae, *Liriomyza trifolii, Liriomyza sativae,* and *Liriomyza bryoniae,* Tephritidae, Phoridae, Drosophilidae, Psychodidae, Simuliidae, Tabanidae, and *Stomoxyini;* Thysanopteran insect pests, for example, *Thrips palmi* Karny, *Frankliniella occidentalis* Pergande, *Thrips tabaci* Lindeman, *Thrips hawaiiensis, Scirtothrips dorsalis, Frankliniella intonsa,* and *Ponticulothrips diospyrosi;* and Plant Parasitic Nematodes, for example, Aphelenchoididae such as *Meloidogyne hapla, Pratylenchus,* Heteroderidae, *Aphelenchoides besseyi,* and *Bursaphelenchus xylophilus.*

Among them, hemipteran insect pests are preferred as insect pests to which the systemic insecticide according to the present invention is applied.

The compounds of formula (1) or salts thereof as such may be used as an active ingredient of the systemic insecticide, but are generally mixed with suitable solid carriers, liquid carriers, gaseous carriers, surfactants, dispersants, or other adjuvants for formulations and formulated into any suitable dosage forms, for example, wettable powders, water dispersible granules, suspensions, flowables, granules, micro granule, dusts, emulsifiable concentrates, EW agents, liquid formulations, tablets, oils, and aerosols, for use as compositions.

Solid carriers include, for example, talc, bentonite, clay, kaolin, diatomaceous earth, vermiculite, zeolite, white carbon, calcium carbonate, acid clay, pumice, attapulgite, and titanium oxide.

Liquid carriers include, for example, alcohols such as methanol, n-hexanol, ethylene glycol, and propylene glycol; ketones such as acetone, methyl ethyl ketone, and cyclohexanone; aliphatic hydrocarbons such as n-hexane, kerosine, and kerosene; aromatic hydrocarbons such as toluene, xylene, and methylnaphthalene; ethers such as diethyl ether, dioxane, and tetrahydrofuran; esters such as ethyl acetate; nitriles such as acetonitrile and isobutyronitrile; acid amides such as dimethylformamide and dimethylacetamide; vegetable oils such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfuric esters, alkyl(aryl)sulfonic acid salts, polyoxyalkylene alkyl(aryl)ethers, polyhydric alcohol esters, dioctyl sodium sulfosuccinate, alkyl maleate copolymer, sodium alkylnaphthalene sulfonate, sodium salts of β-naphthalene sulfonate formaldehyde condensate, lignin sulfonic acid salts, polyoxyethylene tristyryl phenyl ether sulfate, or phosphate.

Adjuvants usable for improving the properties of formulations include, for example, pregelatinized starch, dextrin, carboxymethylcellulose, gum arabic, polyethylene glycol, calcium stearate, polyvinyl pyrrolidone, sodium alginate, phenolic antioxidant, amine antioxidant, phosphorus antioxidant, sulfureous antioxidant, and epoxidized vegetable oil.

The above carriers, surfactants, dispersants, and adjuvants may be used either solely or in combination according to need.

The suitable content of the active ingredient in these formulations is generally 1 to 75% by weight for emulsifiable concentrate, generally 0.3 to 25% by weight for dust, generally 1 to 90% by weight for wettable powder, and generally 0.5 to 10% by weight for granules.

Preferably, the systemic insecticide according to the present invention is applied to seeds, roots, tubers, bulbs, or rhizomes of plants, more preferably seeds of plants. When the plants are an object to which the systemic insecticide is applied, the compounds of formula (1) can be advantageously efficiently absorbed and penetrated into the plants to attain systemic insecticidal effect.

Plants

Plants into which the compound of formula (1) has been systemically translocated as such have insecticidal activity and can be advantageously utilized in the control of insect pests that suck or chew the plants. Thus, according to a further aspect of the present invention, there is provided a plant treated with the systemic insecticide according to the present invention, wherein the plant is selected from seeds, roots, tubers, bulbs, and rhizomes. According to a preferred embodiment, the treatment includes systemic translocation of the compound of formula (1) into the plant Control Method According to another aspect of the present invention, there is provided a method comprising applying an effective amount of one or more compounds of formula (1) or salts thereof to an object selected from the group consisting of soil, nutrient solutions in nutricultures, solid media in nutricultures, and seeds, roots, tubers, bulbs, and rhizomes of plants, and systemically translocating the compound of formula (1) into the plant.

When the object is a seed, root, tuber, bulb, or rhizome of a plant, any application method that does not inhibit systemic translocation of the compound of formula (1) can be adopted without particular limitation, and examples of suitable application methods include dipping, dust coating, smearing, spraying, pelleting, or coating.

According to a preferred embodiment of the present invention, the object is a seed. When the object is a seed, application methods usable herein include dipping, dust coating, smearing, spraying, pelleting, coating, and fumigating. The dipping is a method in which seeds are dipped in a chemical solution. The dust coating is classified into two types, i.e., a dry dust coating method in which a powdery chemical is adhered onto dry seeds, and a wet dust coating method in which a powdery chemical is adhered onto seeds which have been lightly soaked in water. The smearing is a method in which a suspended chemical is coated on the surface of seeds within a mixer. The spraying is a method in which a suspended chemical is sprayed onto the surface of seeds. The pelleting is a method in which a chemical is mixed with a filler when seeds, together with a filler, are pelleted to form pellets having given size and shape. The coating is a method in which a chemical-containing film is coated onto seeds. The fumigating is a method in which seeds are sterilized with a chemical which has been gasified within a hermetically sealed vessel.

The compounds of formula (1) or salts thereof can also be applied to, in addition to seeds, germinated plants which are transplanted after germination or after budding from soil, and embryo plants. These plants can be protected by the treatment of the whole or a part thereof by dipping before transplantation.

The application of the compounds of formula (1) or salts thereof to soil used, for example, in planting of plants is also preferred. Any method for application to soil that does not inhibit the systemic translocation of the compounds of formula (1) may be adopted without particular limitation. Preferred application methods are as follows.

An example of such methods is one in which granules containing a compound of formula (1) or a salt thereof are applied into soil or on soil. Preferred soil application methods include spreading, stripe application, groove application, and planting hole application. The spreading includes surface treatment over the whole area to be treated, and mechanical introduction into soil following the surface treatment.

Drenching of soil with a solution prepared by emulsifying or dissolving the compound of formula (1) or salt thereof in water is also an advantageous soil application method.

Examples of other preferred application methods include application into a nutrient solution in nutrient solution culture systems such as water culture and solid medium culture, for example, sand culture, NFT (nutrient film technique), or rock wool culture, for the production of vegetables and flowering plants. It is also apparent that the compound of formula (1) can be applied directly to artificial culture soil containing vermiculite and a solid medium containing an artificial mat for raising seedling.

In the application step, the effective amount of the compound of formula (1) or salt thereof is preferably an amount large enough to tallow the compound of formula (1) to systemically translocated into the plant in the subsequent systemic translocation step.

The effective amount can be properly determined by taking into consideration, for example, the properties of compounds, the type and amount of the application object, the length of the subsequent systemic translocation step, and the temperature. For example, in the case of seeds, the compound of formula (1) or salt thereof is applied in an amount of preferably 1 g to 10 kg, more preferably 100 g to 1 kg, per 100 kg of seeds. On the other hand, in the case of application to soil, the compound of formula (1) or salt thereof is applied in an amount of preferably 0.1 g to 10 kg, more preferably 1 g to 1 kg, per 10 ares of cultivated land.

In the control method according to the present invention, the compound of formula (1) or salt thereof is applied to the object, followed by systemic translocation of the compound of formula (1) into the plant.

The systemic translocation method is not particularly limited. An example thereof is a method in which a plant such as seed, root, tuber, bulb, or rhizome is planted or dipped in soil or medium to which the compound of formula (1) has been applied, or a chemical solution containing the compound of formula (1) for a period of time long enough to allow the chemical to be systemically translocated into the plant. When the application amount of the chemical and duration sufficient for systemic translocation are selected, the systemic translocation step can also be carried out by applying the compound of formula (1) directly to the plant and allowing the plant to stand still. The present invention includes this embodiment.

The time and temperature in the systemic translocation may be properly determined by a person having ordinary skill in the art depending, for example, upon the object to be applied and the type and amount of the chemical. The systemic translocation time is not particularly limited and may be, for example, one hr or longer. The temperature in the systemic translocation is, for example, 5 to 45° C.

The compounds of formula (1) may be used as a mixture with other chemicals, for example, fungicides, insecticides, miticides, herbicides, plant growth-regulating agents, or fertilizers. Specific examples of other admixable chemicals are described, for example, in The Pesticide Manual, the 13th edition, published by The British Crop Protection Council; and SHIBUYA INDEX, the 10th edition, 2005, published by SHIBUYA INDEX RESEARCH GROUP.

More specific examples of other chemicals include insecticides, for example, acephate, dichlorvos, EPN, fenitothion, fenamifos, prothiofos, profenofos, pyraclofos, chlorpyrifos-methyl, chlorfenvinphos, demeton, ethion, malathion, coumaphos, isoxathion, fenthion, diazinon, thiodicarb, aldicarb, oxamyl, propoxur, carbaryl, fenobucarb, ethiofencarb, fenothiocarb, pirimicarb, carbofuran, carbosulfan, furathiocarb, hyquincarb, alanycarb, benfuracarb, cartap, thiocyclam, bensultap, dicofol, tetradifon, cyromazine, fenoxycarb, dicyclanil, buprofezin, flubendiamide, ethiprole, fipronil, imidacloprid, nitenpyram, clothianidin, acetamiprid, dinotefuran, thiacloprid, thiamethoxam, pymetrozine, flonicamid, spinosad, avermectin, milbemycin, nicotine, emamectinbenzoate, spinetoram, pyrifluquinazon, chlorantraniliprole, spirotetramat, lepimectin, metaflumizone, pyrafluprole, pyriprole, hydramethylnon, and triazamate. Preferred examples thereof include acephate, ethiprole, fipronil, imidacloprid, clothianidin, thiamethoxam, avermectin, and milbemycin. Acephate and imidacloprid are more preferred.

Examples of preferred admixable fungicides include strobilurin compounds such as azoxystrobin, kresoxym-methyl, trifloxystrobin, orysastrobin, picoxystrobin, and fuoxastrobin; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; benzimidazole compounds such as benomyl, thiophanate-methyl, and carbendazole; phenylamide compounds such as metalaxyl, oxadixyl, ofurase, benalaxyl, furalaxyl, and cyprofuram; isoxazole compounds such as hydroxyisoxazole; benzanilide compounds such as flutolanil and mepronil; morpholine compounds such as fenpropimorph and dimethomorph; cyanopyrrole compounds such as fludioxonil and fenpiclonil; and probenazole, acibenzolar-S-methyl, tiadinil, isotianil, carpropamid, diclocymet, fenoxanil, tricyclazole, pyroquilon, ferimzone, fluazinam, cymoxanil, triforine, pyrifenox, fenarimol, fenpropidin, pencycuron, cyazofamid, cyflufenamid, boscalid, penthiopyrad, proquinazid, quinoxyfen, famoxadone, fenamidone, iprovalicarb, benthiavalicarb-isopropyl, fluopicolide, pyribencarb, kasugamycin, or validamycin. Particularly preferred examples thereof include strobilurin compounds, azole compounds, and phenylamide compounds.

EXAMPLES

The present invention is further illustrated by the following Examples that are not intended as a limitation of the invention. Compound 4 in the Examples was synthesized by the process described in WO 2006/129714.

Synthetic Examples

Synthetic Example 1

Compound 5

PR-3 (20 mg) synthesized by the process described in Japanese Patent Application Laid-Open No. 259569/1996 and cyclopropanecarboxylic acid (19 mg) were dissolved in anhydrous N,N-dimethylformamide (1 ml), and 1-ethyl-3-(3-dimethylaminopropyl)-carbodiimide hydrochloride (84 mg) and 4-(dimethylamino)pyridine (5 mg) were added to the solution. The mixture was stirred at room temperature for 6 hr. The reaction solution was poured into water, and the mixture was extracted with ethyl acetate. The ethyl acetate layer was washed with saturated brine and was dried over anhydrous magnesium sulfate, and the solvent was removed by evaporation under the reduced pressure to give a crude product of compound 5. The crude product was purified by preparative thin-layer column chromatography (Merck silica gel 60F$_{254}$ (0.5 mm), chloroform:methanol=10:1) to give compound 5 (9.0 mg).

Synthetic Example 2

Compound 6

[Chemical formula 2]

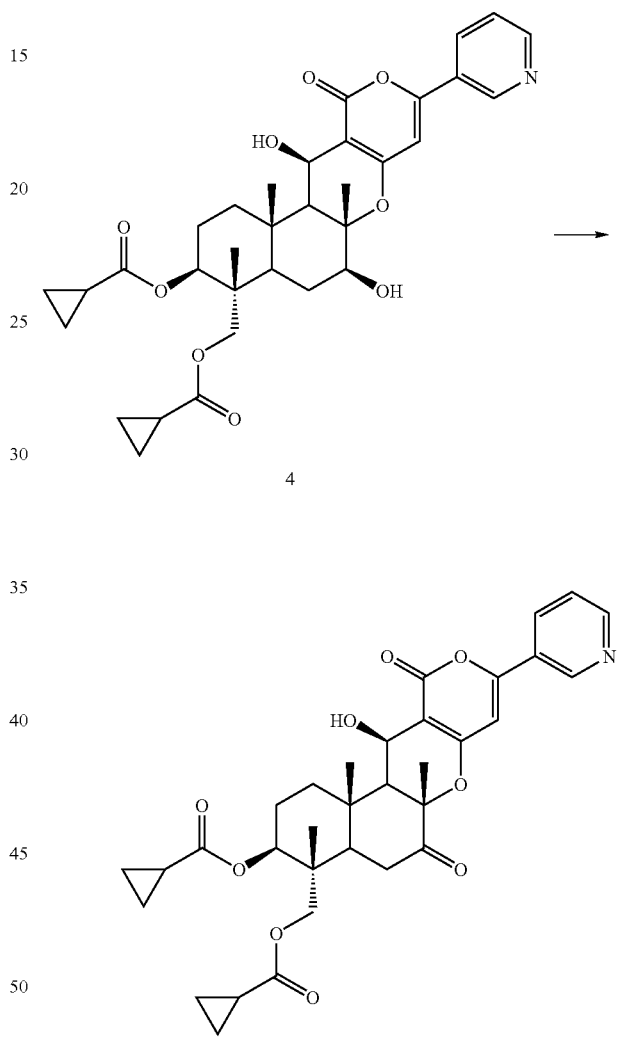

Compound 4 (20 mg) was dissolved in dichloromethane (1 ml). Dess-Martin periodinane (21 mg) was added to the solution at 0° C., and, in this state, the mixture was stirred for 2 hr 40 min. A saturated aqueous sodium thiosulfate solution was added to the reaction solution, and the mixture was extracted with chloroform. The chloroform layer was washed with saturated brine and was dried over anhydrous magnesium sulfate. The solvent was then removed by evaporation under the reduced pressure, and the crude product thus obtained was purified by preparative thin-layer chromatography (Merck silica gel 60 F$_{254}$ (0.5 mm), acetone:hexane=1:1) to give compound 6 (5.4 mg).

Synthetic Example 3

Compound 7

[Chemical formula 3]

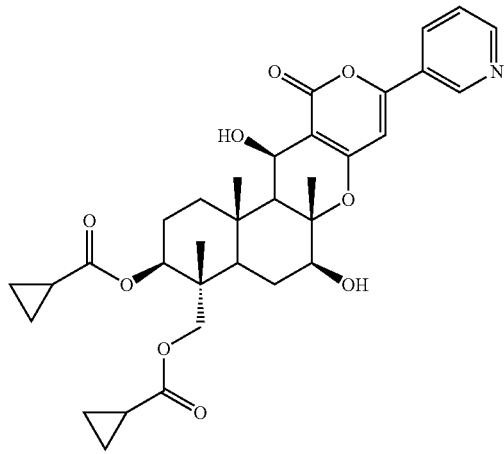

4

[Chemical formula 4]

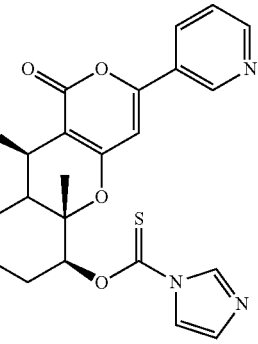

a

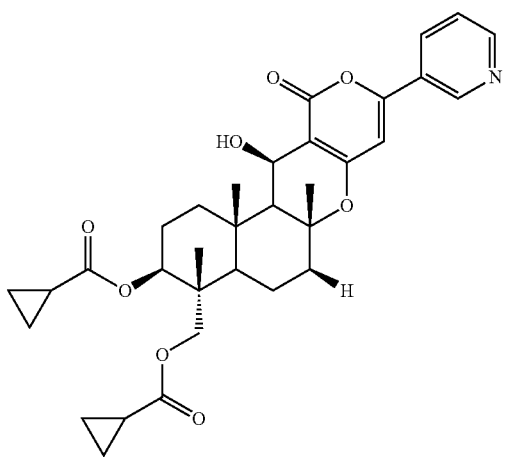

7

Compound 4 (50 mg) was dissolved in toluene (3 ml). 1,1'-Thiocarbonyldiimidazole (90 mg) was added to the solution at room temperature, and the mixture was heated under reflux for 2.5 hr. The reaction solution was cooled to room temperature. Water was added to the reaction solution, and the mixture was extracted with ethyl acetate. The ethyl acetate layer was washed with saturated brine and was dried over anhydrous magnesium sulfate, and the solvent was then removed by evaporation under the reduced pressure. The crude product thus obtained was purified by preparative thin-layer chromatography (Merck silica gel 60 $F_{254}$ (0.5 mm), acetone:hexane=1:1) to give compound a (41.1 mg).

Compound a (41 mg) was dissolved in toluene (2 ml). Tri-n-butyl tin hydride (20 mg) was added to the solution at room temperature, and the mixture was heated under reflux for 2.5 hr. The reaction solution was cooled to room temperature. Water was added to the reaction solution, and the mixture was extracted with ethyl acetate. The ethyl acetate layer was washed with saturated brine and was dried over anhydrous magnesium sulfate, and the solvent was then removed by evaporation under the reduced pressure. The crude product thus obtained was purified by preparative thin-layer chromatography (Merck silica gel 60 $F_{254}$ (0.5 mm), acetone:hexane=1:1) to give compound 7 (3.5 mg).

$^1$H-NMR data and mass spectrometric data for compounds 5, 6, and 7 were as shown in Table 2.

TABLE 2

| Compound | Solvent | NMR data<br>$^1$H-NMR δ(ppm) | Mass spectrometric data | |
|---|---|---|---|---|
| | | | Measuring method | Data |
| 5 | CDCl$_3$ | 0.83 (3H, s), 0.88-0.95 (2H, m), 1.00-1.08 (2H, m), 1.26 (1H, m), 1.33 (1H, m), 1.40 (3H, s), 1.43 (1H, m), 1.57-1.74 (2H, m), 1.67 (3H, s), 1.79-1.88 (2H, m), 1.93 (1H, m), 2.15 (1H, m), 2.97 (1H, s), 3.41 (1H, dd, J = 5.2, 11.2 Hz), 3.75 (1H, d, J = 11.6 Hz), 3.82 (1H, dd, J = 5.2, 11.6 Hz), 4.28 (1H, d, J = 11.6 Hz), 5.00 (1H, d, J = 4.0 Hz), 6.53 (1H, s), 7.43 (1H, dd, J = 4.4, 8.0 Hz), 8.12 (1H, dt, J = 8.4 Hz), 8.70 (1H, m), 9.02 (1H, m) | ESI | 528 (M + H)$^+$ |
| 6 | CDCl$_3$ | 0.83-1.00 (8H, m), 0.96 (3H, s), 1.44 (1H, m), 1.53-1.61 (2H, m), 1.63 (3H, s), 1.76 (1H, d, J = 3.7 Hz), 1.81 (3H, s), 1.87 (2H, m), 1.94-1.97 (1H, m), 2.21 (1H, m), 2.53 (1H, dd, J = 2.6, 14.9 Hz), 2.78 (1H, t, J = 14.9 Hz), 2.91 (1H, d, J = 1.5 Hz), 3.66 (1H, d, J = 12.0 Hz), 3.84 (1H, d, J = 12.0 Hz), 4.82 (1H, dd, J = 4.8, 11.7 Hz), 5.06 (1H, m), 6.71 (1H, s), 7.41 (1H, dd, J = 4.8, 8.0 Hz), 8.09 (1H, dt, J = 1.7, 8.0 Hz), 8.70 (1H, dd, J = 1.7, 4.8 Hz), 9.02 (1H, d, J = 1.7 Hz) | ESI | 592 (M + H)$^+$ |
| 7 | CDCl$_3$ | 0.84-1.00 (8H, m), 0.90 (3H, s), 1.12-1.16 (1H, m), 1.25 (1H, s), 1.35-1.46 (1H, m), 1.41 (3H, s), 1.56-1.70 (5H, m), 1.66 (3H, s), 1.78-1.89 (2H, m), 2.12-2.17 (2H, m), 2.82 (1H, d, J = 1.4 Hz), 3.69 (1H, d, J = 11.9 Hz), 3.91 (1H, d, J = 11.9 Hz), 4.83 (1H, dd, J = 5.1, 11.5 Hz), 4.99 (1H, m), 6.46 (1H, s), 7.42 (1H, m), 8.11 (1H, dt, J = 1.7, 8.0 Hz), 8.69 (1H, m), 9.01 (1H, m) | ESI | 578 (M + H)$^+$ |

Formulation Examples

Formulation Example 1

Granules

| | |
|---|---|
| Compound 4 | 0.5% by weight |
| Alkyl sulfate | 0.2% by weight |
| Pregelatinized starch | 5% by weight |
| Clay | 94.3% by weight |

The ingredients were homogeneously ground and mixed together, water was added to the mixture, and the mixture was thoroughly kneaded, granulated, and dried to prepare 0.5% granule.

Formulation Example 2

Wettable Powder

| | |
|---|---|
| Compound 4 | 5% by weight |
| Sodium lauryl sulfate | 1% by weight |
| White carbon | 5% by weight |
| Clay | 80% by weight |
| Sodium lignosulfate | 9% by weight |

The ingredients were homogeneously mixed together and ground to prepare a 5% wettable powder.

Formulation Example 3

Water Dispersible Granule

| | |
|---|---|
| Compound 4 | 20% by weight |
| Alkyl sulfate | 0.5% by weight |
| Clay | 68.5% by weight |
| Dextrin | 5% by weight |
| Alkylmaleic acid copolymer | 6% by weight |

The ingredients were homogeneously ground and mixed together. Water was added to the mixture, followed by thorough kneading. Thereafter, the kneaded product was granulated and dried to prepare a 20% water dispersible granule.

Formulation Example 4

Flowables

| | |
|---|---|
| Compound 4 | 5% by weight |
| Sodium lignosulfate | 6% by weight |
| Propylene glycol | 7% by weight |
| Bentonite | 1.5% by weight |
| 1% Aqueous xanthan gum solution | 1% by weight |
| Silicone antifoam KM-98 | 0.05% by weight |
| Water | To 100% by weight |

All the ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100% by weight flowables.

Formulation Example 5

Emulsifiable Concentrate

| Compound 4 | 1% by weight |
| Solvesso 150 (Exxon Mobil Corporation) | 82.5% by weight |
| Tayca Power BC2070M | 8.25% by weight |
| SORPOL CA-42 | 8.25% by weight |

The above ingredients were homogeneously mixed together and dissolved to prepare an emulsifiable concentrate.

Test Examples

<Soil Irrigation Treatment Test>

Test Example 1

Insecticidal Effect Against *Aphis gossypii*

Cucumber seedlings were treated by soil drenching treatment with a diluted solution of the formulation adjusted to a predetermined concentration with water. The chemical was absorbed through the root for six days, and five adult *Aphis gossypii* for each seedling were then released. Thereafter, the seedlings were allowed to stand in a thermostatic chamber of 25° C. The number of parasites on leaves was observed six days after the release, and the density index was calculated by the following equation.

Density index=(number of parasites in treated plot/
number of parasites in non-treated plot)×100

As shown in Table 3, the 5% wettable powder, 20% water dispersible granule, and 0.5% granule each containing compound 4 prepared as described respectively in Formulation Example 2, Formulation Example 3, and Formulation Example 1 had systemically high density inhibitory effect against *Aphis gossypii*.

TABLE 3

Effect of formulation containing compound 4 against *Aphis gossypii*

| Name of formulation | Treatment amount (mg of original substance/root) | Density index 6 days after release |
|---|---|---|
| 5% Wettable powder | 10 | 0 |
| 20% Water dispersible granule | 10 | 0 |
| 0.5% Granule | 10 | 0 |

Test Example 2

Insecticidal Effect Against *Myzus persicae* Sulzer

Eggplant seedlings were treated by soil drenching treatment with a diluted solution of the formulation adjusted to a predetermined concentration with water. The chemical was absorbed through the root for five days, and three adult *Myzus persicae* Sulzer for each seedling were then released. Thereafter, the seedlings were allowed to stand in a thermostatic chamber of 25° C. The number of parasites on leaves was observed five days after the release, and the density index was calculated by the same equation as in Test Example 1. The test was duplicated.

As shown in Table 4, the wettable powder containing compound 4 prepared as described in Formulation Example 2 had systemically high density inhibitory effect against *Myzus persicae* Sulzer.

TABLE 4

Effect of formulation containing compound 4 against *Myzus persicae* Sulzer

| Name of formulation | Treatment amount (mg of original substance/root) | Density index 5 days after release |
|---|---|---|
| 5% Wettable powder | 5.0 | 2.4 |

<Root Soaking Treatment Test>

Test Example 3

Insecticidal Effect Against *Rhopalosiphum padi*

The root of wheat seedlings 48 hr after seeding was soaked for 72 hr in a test solution (100 ppm) prepared as a 10% aqueous acetone solution. 72 hrs after the treatment, 10 larval *Rhopalosiphum padi* were released for each seedling. Thereafter, the seedlings were allowed to stand in a thermostatic chamber of 25° C. The number of parasites on stems and leaves was observed six days after the release, and the density index was calculated by the same equation as in Test Example 1. The test was duplicated.

As a result, as shown in Table 5, compounds 1, 2, 3, 4, 5, 6, and 7 described in Table 1 had systemically high density inhibitory effect against *Rhopalosiphum padi*.

TABLE 5

Effect of compounds 1 to 7 against *Rhopalosiphum padi*

| Compound No. | Treatment concentration (μg/seedling) | Density index 6 days after release |
|---|---|---|
| 1 | 20 | 20 |
| 2 | 20 | 0 |
| 3 | 20 | 18 |
| 4 | 20 | 5 |
| 5 | 20 | 0 |
| 6 | 20 | 0 |
| 7 | 20 | 41 |

Comparative Tests: Insecticidal Effect Against *Rhopalosiphum padi*

For compounds 8 and 9 described in Table 6, a insecticidal effect against *Rhopalosiphum padi* was examined in the same manner as in Test Example 3. As a result, as shown in Table 7, compounds 8 and 9 did not have a density inhibitory effect.

In Table 6, substituents $R_1$, $R_2$, and $R_3$ correspond respectively to substituents $R_1$, $R_2$, and $R_3$ in formula (1).

TABLE 6

Comparative test compounds

| Compound No. | $R_1$ | $R_2$ | $R_3$ |
|---|---|---|---|
| 8 | $OCOCH_2CH_3$ | $OCOCH_2CH_3$ | $OCOCH_2CH_3$ |
| 9 | OCO-phenyl | OCO-phenyl | OCO-phenyl |

TABLE 7

Effect of compounds 8 and 9 against *Rhopalosiphum padi*

| Compound No. | Treatment concentration (μg/seedling) | Density index 6 days after release |
|---|---|---|
| 8 | 20 | 95 |
| 9 | 20 | 95 |

Reference Test: Insecticidal Effect Against *Myzus persicae* Sulzer

A leaf disk having a diameter of 2.8 cm was cut out from a cabbage grown in a pot and was placed in a 5.0 cm-Schale. Four adult aphids of *Myzus persicae* Sulzer were released in the Schale. One day after the release of the adult aphids, the adult aphids were removed. The number of larvae at the first instar born in the leaf disk was adjusted to 10, and 20 ppm of a test solution which had been prepared as a 50% aqueous acetone solution (0.05% Tween 20 added) was spread over the cabbage leaf disk. The cabbage leaf disk was then air dried. Thereafter, the Schale was lidded and was allowed to stand in a thermostatic chamber of 25° C. Three days after the release, the larvae were observed for survival or death, and the mortality of larvae was calculated by the following equation.

Mortality (%)={number of dead larvae/(number of survived larvae+number of dead larvae)}×100

As a result, it was found that, for all of compounds 1, 2, 3, 4, 5, 6, 7, 8, and 9 described in Table 1 or 6, spraying treatment exhibited a high insecticidal effect of 100% in terms of mortality.

<Seed Treatment Test>

Test Example 4

Insecticidal Effect Against *Rhopalosiphum padi*

Seeds of wheat were soaked for 6 hr in a diluted solution of the formulation adjusted to a predetermined concentration with water. The seeds were germinated in a thermostatic chamber for 3 days, and the seedlings were transplanted into soil. Two days after the transplantation, 10 larvae of *Rhopalosiphum padi* for each seedling were released. Thereafter, the seedlings were allowed to stand in a thermostatic chamber of 25° C. 6 days after the release, the number of parasites on the stems and leaves was observed, and the density index was calculated by the same equation as in Test Example 1. The test was triplicated.

As shown in Table 8, the 5% wettable powder containing compound 4 had high density inhibitory effect against *Rhopalosiphum padi*.

TABLE 8

Effect of formulation containing compound 4 against *Rhopalosiphum padi*

| Name of formulation | Treatment concentration (ppm of original substance) | Density index 6 days after release |
|---|---|---|
| 5% Wettable powder | 500 | 4.1 |

<Soil Drenching Treatment Test>

Test Example 5

Insecticidal Effect Against *Trialeurodes uaporariorum*

Adults of *Trialeurodes uaporariorum* were released on cucumber seedlings, grown in a pot, for egg laying purposes for two days. 10 days after the start of egg laying, it was confirmed that larvae were hatched from the delivered eggs. The soil in the cucumber pot was drenched with 5 mL of a test solution adjusted to a predetermined concentration with a 10% aqueous acetone solution. The cucumber pot was allowed to stand in a thermostatic chamber of 25° C. (light period 16 hr-dark period 8 hr). 9 days after the drenching, the number of survived larvae was measured, and the mortality of larvae was calculated by the following equation. The test was duplicated.

Mortality (%)={(number of larvae before treatment−number of survived larvae)/number of larvae before treatment}×100

As shown in Table 9, compound 4 had high systemic insecticidal activity against *Trialeurodes uaporariorum*.

Test Example 6

Insecticidal Effect Against *Laodelphax stratella*

Rice seedlings grown in a pot were provided. Soil in the pot was drenched with a test solution adjusted to a predetermined concentration with a 10% aqueous acetone solution. After standing for three days, 10 larvae at the second instar were released on the rice seedlings. Thereafter, the pot was allowed to stand in a thermostatic chamber of 25° C. (light period 16 hr-dark period 8 hr). 3 days after the release, the number of survived larvae was measured, and the mortality of larvae was calculated by the same equation as in the Reference Test. The test was duplicated.

As shown in Table 9, compound 4 had high systemic insecticidal activity against *Laodelphax stratella*.

Test Example 7

Insecticidal Effect Against *Nephotettix cincticeps*

Rice seedlings grown in a pot were provided. Soil in the pot was drenched with a test solution adjusted to a predetermined concentration with a 10% aqueous acetone solution. After standing for three days, 10 larvae at the second instar were released on the rice seedling. Thereafter, the pot was allowed to stand in a thermostatic chamber of 25° C. (light period 16 hr-dark period 8 hr). 3 days after the release, the number of survived larvae was measured, and the mortality of larvae was calculated by the same equation as in the Reference Test. The test was duplicated.

As shown in Table 9, compound 4 had high systemic insecticidal activity against *Nephotettix cincticeps*.

TABLE 9

Insecticidal activity of compound 4 against various insect pests

| Pest name | Treatment amount (mg/seedling) | Mortality (%) |
|---|---|---|
| *Trialeurodes uaporariorum* | 0.5 | 67 |
| *Laodelphax stratella* | 0.5 | 34 |
| *Nephotettix cincticeps* | 1.0 | 60 |

The treatment amount is expressed in terms of original substance.

<Test Example of Soil Drenching Treatment Using>Insecticidal Admixture

Test Example 8

Insecticidal effect against *Aphis gossypii*

Cucumber seedlings were treated by soil drenching with a single agent and an admixture adjusted to a predetermined concentration with water. The chemical was absorbed through the root for two days, and four adults of *Aphis gossypii* for each seedling were released on the seedlings. Thereafter, the seedlings were allowed to stand in a thermostatic chamber of 25° C. 2 days after the release, the number of parasites on the leaves was observed. The density index in each treated plot was determined by presuming the density in the non-treated plot to be 100. The preventive value was calculated by the following equation.

Preventive value=100−density index

The results were as shown in Table 10. When the density index exceeded 100, the preventive value was regarded as 0 (zero).

Further, theoretical values, which do not exhibit a synergistic effect, were calculated by the following Colby's formula, and the results are shown in Table 11.

Theoretical value=$A+B-(A\times B)/100$        Colby's formula where A: preventive value when treatment was performed only with compound 4, and B: preventive value when treatment was performed only with each of acephate and imidacloprid.

Method for Determining Synergistic Effect

When the numerical value for the admixture in Table 10 exceeded the theoretical value calculated by the Colby's formula shown in Table 11, the admixture was determined to have a synergistic effect.

All the tested admixtures had preventive values beyond the theoretical values, demonstrating that they had a synergistic effect.

TABLE 10

Preventive value of single agent and admixture against *Aphis gossypii*

| Other insecticide | Compound 4 0 mg/seedling | 0.05 mg/seedling |
|---|---|---|
| — | 0 | 0 |
| Acephate 0.1 mg/seedling | 70 | 100 |
| Imidacloprid 0.005 mg/seedling | 16 | 43 |

The treatment amount is expressed in terms of original substance.

TABLE 11

Theoretical value calculated by Colby's formula

| Other insecticide | Compound 4 0 mg/seedling | 0.05 mg/seedling |
|---|---|---|
| — | 0 | 0 |
| Acephate 0.1 mg/seedling | 70 | 70 |
| Imidacloprid 0.005 mg/seedling | 16 | 16 |

The treatment amount is expressed in terms of original substance.

Test Example 9

Insecticidal Effect Against *Rhopalosiphum padi*

The root of wheat seedlings 48 hr after seeding was soaked for 72 hr in an admixture solution, adjusted to a predetermined concentration, as a 10% aqueous acetone solution. 72 hrs after the treatment, 10 larval *Rhopalosiphum padi* for each seedling were released on the seedlings. Thereafter, the seedlings were allowed to stand in a thermostatic chamber of 25° C. The number of parasites on stems and leaves was observed six days after the release. The density index of each of the treated plots was determined by presuming the density of the non-treated plots to be 100, and the preventive value was calculated by the same equation as in Test Example 8.

The results are shown in Table 12. When the density index exceeded 100, the preventive value was regarded as 0 (zero).

Theoretical values, which do not exhibit a synergistic effect, were calculated by the following Colby's formula, and the results are shown in Table 13.

Theoretical value=$A+B-(A\times B)/100$        Colby's formula where A: preventive value when treatment was performed only with compound 4, and B: preventive value when treatment was performed only with each of acetamiprid, acephate, and imidacloprid.

Method for Determining Synergistic Effect

When the preventive value against *Rhopalosiphum padi* for the admixture in Table 12 exceeded the theoretical value calculated by the Colby's formula shown in Table 13, the admixture was determined to have a synergistic effect. All the tested admixtures had preventive values beyond the theoretical values, demonstrating that they had a synergistic effect.

TABLE 12

Preventive value of single agent and admixture against *Rhopalosiphum padi*

| Other Compound 4 insecticide | 0 μg/seedling | 0.5 μg/seedling |
|---|---|---|
| — | 0 | 0 |
| Acetamiprid 0.0078 μg/seedling | 5.9 | 40.0 |
| Acephate 0.5 μg/seedling | 55.6 | 100 |
| Imidacloprid 0.0078 μg/seedling | 28.6 | 54.5 |

The treatment amount is expressed in terms of original substance.

TABLE 13

Theoretical value calculated by Colby's formula

| Other Compound 4 insecticide | 0 μg/seedling | 0.5 μg/seedling |
|---|---|---|
| — | 0 | 0 |
| Acetamiprid 0.0078 μg/seedling | 5.9 | 5.9 |
| Acephate 0.5 μg/seedling | 55.6 | 55.6 |
| Imidacloprid 0.0078 μg/seedling | 28.6 | 28.6 |

The treatment amount is expressed in terms of original substance.

Test Example 10

Insecticidal Effect Against *Laodelphax stratella*

Rice seedlings grown in a pot were treated by soil drenching with a single agent or an admixture adjusted to a predetermined concentration with water. The seedlings were allowed to stand for two days. Ten larvae at the second instar were released on the rice seedlings. Thereafter, the rice seedlings were allowed to stand in a thermostatic chamber of 25° C. (light period 16 hr-dark period 8 hr). 4 days after the release, the number of survived larvae was observed, and the mortality of larvae was calculated by the same equation as in the Reference Test. The test was duplicated.

The results are shown in Table 14.

Theoretical values, which do not exhibit a synergistic effect, were calculated by the following Colby's formula, and the results are shown in Table 15.

Theoretical value (%)=100−($A \times B$)/100    Colby's formula where A: 100—(mortality when treatment was performed only with compound 4), and B: 100—(mortality when treatment was performed only with imidacloprid).

Method for Determining Synergistic Effect

When the numerical value for the admixture in Table 14 exceeded the theoretical value calculated by the Colby's formula shown in Table 15, the admixture was determined to have a synergistic effect.

The tested admixture had mortalities beyond the theoretical values, demonstrating that they had a synergistic effect.

TABLE 14

Mortality (%) of single agent and admixture against *Laodelphax stratella*

| Wettable powder containing Other compound 4 insecticide | 0 mg/seedling | 1.0 mg/seedling |
|---|---|---|
| — | 0 | 57 |
| Admire wettable powder 0.01 mg/seedling | 60 | 93 |

The treatment amount is expressed in terms of original substance.

TABLE 15

Theoretical value (%) calculated by Colby's formula

| Wettable powder containing Other compound 4 insecticide | 0 mg/seedling | 1.0 mg/seedling |
|---|---|---|
| — | 0 | 57 |
| Admire wettable powder 0.01 mg/seedling | 60 | 83 |

The treatment amount is expressed in terms of original substance.

The invention claimed is:

1. A method for controlling agricultural or horticultural insect pests which suck or chew a plant, comprising:
applying at least one compound represented by formula (1) or a salt thereof to an object selected from the group consisting of a seed, root, tuber, bulb, and rhizome of the plant, in an amount effective to systemically translocate the compound into the plant,

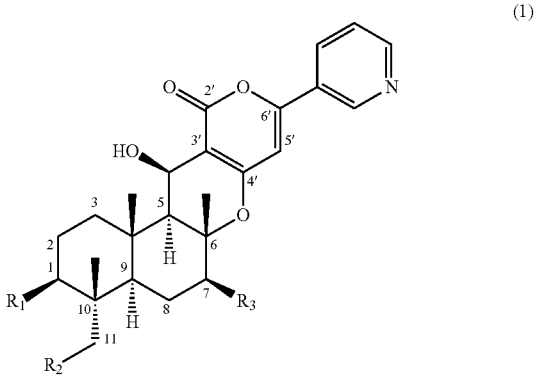

(1)

wherein:
$R_1$ and $R_2$ represent optionally substituted $C_{3-4}$ cyclic alkylcarbonyloxy; and $R_3$ represents hydroxyl; and
systemically translocating the compound into the plant to be sucked or chewed by the insect pests, wherein the systemic translocation comprises dipping or soaking the object in a solution or medium, which contains the at least one compound represented by formula (1) or a salt thereof, for at least 6 hours.

2. A plant treated with the at least one compound of formula (1) or a salt thereof according to claim 1, wherein the plant is selected from the group consisting of a seed, root, tuber, bulb, and rhizome.

3. The method according to claim 1, wherein the object is the seed of a plant, and the at least one compound of formula (1) or salt thereof is applied in an amount of 1 g to 10 kg per 100 kg of the seed.

4. The method according to claim 1, wherein the object is planted in the soil or on the soil after dipping or soaking of the object in the solution.

5. The method according to claim 4, wherein the at least one compound of formula (1) or salt thereof is applied in an amount of 0.1 g to 10 kg per 10 ares of arable land.

* * * * *